United States Patent [19]

Arditi

[11] Patent Number: 5,526,816
[45] Date of Patent: Jun. 18, 1996

[54] ULTRASONIC SPECTRAL CONTRAST IMAGING

[75] Inventor: Marcel Arditi, Geneva, Switzerland

[73] Assignee: Bracco Research S.A., Carouge-Geneve, Switzerland

[21] Appl. No.: 460,258

[22] Filed: Jun. 2, 1995

[30] Foreign Application Priority Data

Sep. 22, 1994 [EP] European Pat. Off. .............. 94810546

[51] Int. Cl.$^6$ ...................................................... A61B 8/00
[52] U.S. Cl. ...................................................... 128/662.02
[58] Field of Search .......................... 128/660.06, 660.07, 128/660.08, 662.02; 73/625, 626, 602; 364/413.25

[56] References Cited

U.S. PATENT DOCUMENTS 5,255,683  10/1993  Monaghan .
5,313,948  5/1994  Murashita et al. ................. 128/662.02

FOREIGN PATENT DOCUMENTS

3643548A1  12/1986  Germany .

Primary Examiner—George Manuel
Attorney, Agent, or Firm—Nixon & Vanderhye

[57] ABSTRACT

Echographic imaging (such as used for medical diagnosis) uses the injection of specific contrast agents in the body, or more generally in the region to be imaged. Different frequency dependent echographic behavior of the ultrasound contrast agents containing microbubbles as compared to echographic behavior of tissue without contrast agents is exploited by providing separated spectral echo responses and then combining them in ways to enhance image contrast. These imaging principles exploit certain physical "signatures" of the contrast agent responses, allowing increased contrast with respect to tissue background. This contrast enhancement is much larger than what is determined from direct echo amplitude monitoring.

42 Claims, 3 Drawing Sheets

ULTRASONIC SPECTRAL CONTRAST IMAGING

BACKGROUND OF THE INVENTION

1. Field of the Invention

This invention relates to method and apparatus (and use of same) for ultrasound imaging of organs and tissue by detection of ultrasound backscatter from a body region containing a contrast agent.

2. Related Art

Ultrasound tissue imaging typically involves projecting an ultrasound acoustic beam from a transceiver transducer probe to a zone of tissue to be imaged, receiving (via such transceiver transducer probe) the acoustic echo reflected from the tissue as an ultrasound response signal (sometimes referred to as a "radiofrequency" response signal), processing the radiofrequency response into a video output signal in suitable signal processing circuits, storing the video output for visual display in a video scan converter, and scanning the entire tissue image region in this manner to produce a video image of the region under investigation on a display device.

Wide acceptance of ultrasound as an inexpensive non-invasive diagnostic technique coupled with rapid development of electronics and related technology has brought about numerous improvements to ultrasound equipment and ultrasound signal processing circuitry. Ultrasound scanners designed for medical or other uses have become cheaper, easier to use, more compact, more sophisticated and more powerful instruments. However, the changes of acoustic impedance occurring within living tissue are small and the absorption of ultrasound energy by different types of tissue (blood vessels, organs, etc.) are such that diagnostic applications do not always follow technical developments.

This situation changed considerably with the development and introduction of administrable ultrasound contrast agents. Introduction of contrast agents made from suspensions of gas microbubbles or microballoons into organs to be investigated have demonstrated that better ultrasound images of organs and surrounding tissue may be obtained with standard ultrasound equipment. Thus, organs like the liver, spleen, kidneys, heart or other soft tissue have become more clearly visible, which opened up new diagnostic areas for both B-mode and Doppler ultrasound and broadened the use of ultrasound as a diagnostic tool.

Unfortunately, so far, ultrasound contrast agents and ultrasound techniques i.e., scanners, electronic circuitry, transducers and other hardware have rarely been studied and developed together. Almost independent developments of these otherwise related segments of the field resulted in incremental improvements of the respective products and systems; however, this has provided no opportunity to draw on synergies offered by studies in which the electronic/ultrasound characteristics of the apparatus and the physical properties of the contrast agent are combined. A few isolated examples of such studies reported improvements for specific agents/equipment combinations, however, the solutions reported are too limited. More universal methods for producing greater tissue resolution, better image and greater versatility of ultrasound as a diagnostic technique would be welcomed and, provided their implementation is kept relatively simple, would be widely accepted.

Thus a large number of documents describe various developments in the field of medical ultrasound apparatus and imaging, as for example U.S. Pat. No. 4,803,993, U.S. Pat. No. 4,803,994, U.S. Pat. No. 4,881,549, U.S. Pat. No. 5,095,909, U.S. Pat. No. 5,097,836, etc. However, although these documents deal with realtime systems and methods, they do not take into consideration physical properties of the contrast agent. In fact they are not concerned with the contrast agent at all.

An attempt towards improved ultrasound imaging using contrast agents is described in WO-A-93/12720 and/or its U.S. counterpart U.S. Pat. No. 5,255,683 (Monaghan) which discloses a method of imaging a region of the body based on subtracting non-displayed ultrasound "images" obtained prior to injection of a contrast agent from the non-displayed "images" of the same region obtained following administration of the contrast agent. Based on this response subtraction principle, the method performs superposition of images obtained from the same region prior to and after administration of the contrast agent, providing an image of the region perfused by the contrast agent freed from background image, noise and artifacts. In theory, the method described is capable of providing good quality images with enhanced contrast.

However, in practice, such image substraction processing techniques require maintenance of the same reference position of the region imaged for a long period of time, i.e., long enough to allow injection and perfusion of the contrast agent and maintenance and processing of an enormous amount of data. Therefore practical implementation of the Monaghan method is very difficult if not impossible. The difficulty is partly due to inevitable internal body movements related to breathing, digestion and heart beat, and partly due to movements of the imaging probe by the ultrasound operator. Most realtime imaging probes are commonly handheld for best perception, feedback and diagnosis.

Although at one point Monaghan suggests forming one or both of the non-displayed "images" to be subtracted by comparing ratios of echo signal components at different frequencies, he never suggests display of such an "image" itself as being useful or advantageous.

Interesting proposals for improved imaging of tissue containing microbubble suspensions as contrast agent have been made by Burns, P., Radiology 185 P (1992) 142 and Schrope, B. et al., Ultrasound in Med. & Biol. 19 (1993) 567. There, it is suggested that second harmonic frequencies generated by non-linear oscillation of microbubbles be used as Doppler imaging parameters. The method proposed is based on the fact that normal tissue does not display non-linear responses the same way as microbubbles, and therefore the use of second harmonics allows for contrast enhancement between tissue with and without contrast agent. Although attractive, the method has its shortcomings, as its application imposes several strict requirements.

Firstly, excitation of the fundamental "bubble-resonance" frequency must be achieved by fairly narrow-band pulses, i.e., relatively long tone bursts of several cycles. While this requirement is compatible with the circuits and conditions required by Doppler processing, it becomes inapplicable in the case of B-mode imaging, where the ultrasound pulses necessarily are of very short duration, typically one-half or one-cycle excitation. In this case, insufficient energy is converted from the fundamental frequency to its "second-harmonic," and thus the B-mode imaging mode can hardly be used for this echo-enhancing method.

Secondly, the generated second harmonic is attenuated, as the ultrasound echo propagates in tissue on its way back to the transducer, at a rate determined by its frequency, i.e., at a rate significantly higher than the attenuation rate of the fundamental frequency. This constraint is a drawback of the "harmonic-imaging" method, which is thus limited to propagation depths compatible with ultrasound attenuation at the high "second-harmonic" frequency.

Furthermore, in order to generate echo-signal components at twice the fundamental frequency, "harmonic imaging" requires non-linear oscillation of the contrast agent. Such behavior requires the ultrasound excitation level to exceed a certain acoustic threshold at the point of imaging (i.e. at a certain depth in tissue). During non-linear oscillation, a frequency conversion takes place, causing part of the acoustic energy to be converted from the fundamental excitation frequency up to its second harmonic. On the other hand, that level should not exceed the microbubble burst level at which the micro-bubbles are destroyed, and hence harmonic imaging will fail due to the destruction of contrast agent in the imaging volume.

The above constraints to second harmonic imaging methods thus require that the imaging-instrument is set-up in such a way as to ensure the transmit-acoustic level to fall within a certain energy band: high enough to generate second harmonic components, but low enough to avoid microbubble destruction within a few cycles.

Thus in contrast with these "before" and "after" methods, a method which would treat electronic signals originating from realtime echoes obtained simultaneously and during normal real time ("on the fly") applications would provide a great step is towards better imaging and wider use of ultrasound diagnostic equipment. Such method would be based on an enhancement of echo signals received from regions imaged by signal processing functions which are designed to enhance contrast between regions containing contrast agent from those without contrast agent, on the basis of frequency-response parameters, and would be simple to use and implement in new instrument designs.

BRIEF SUMMARY OF THE INVENTION

Briefly summarized, the invention provides a realtime method of ultrasonic imaging of organs and tissue by detection of ultrasound backscatter of a region containing a contrast agent by projecting an ultrasound beam to a zone of the tissue to be imaged and receiving the echo as radiofrequency response signal(s) reflected by the tissue, demodulating the radiofrequency response into a video output signal, storing the output in a video scan converter, scanning the tissue and repeating the above steps to produce a video image of the region under investigation. An important part of the method is in the demodulation step, which includes:

(a) selecting at least two frequencies chosen to enhance the difference between contrast agent responses and tissue responses (e.g., in the range between about the lower bound of the 6 dB amplitude bandwidth of the contrast agent response and about the upper bound of the 6 dB amplitude bandwidth of the tissue response-or between a lower bound of the 6 dB amplitude bandwidth of the tissue response and the upper band of the 6 dB amplitude bandwidth of the contrast agent response), (b) passing the signal to at least two independent channels with pass-bands tuned at the selected frequencies, and (c) demodulating the signals of each of the independent channels.

Upon demodulation, the signals are processed into a single output signal, where echoes reflected by the contrast agent present in the tissue are significantly enhanced in comparison to those reflected by tissue itself.

The invention also provides a system for ultrasonic imaging of organs and tissue by detection of ultrasound backscatter of a region containing a contrast agent, the system including an ultrasonic probe for transmitting and receiving ultrasonic signals, signal processing circuits, means for storing the processed signals and a display element, in which the signal processing circuits separate the signal into at least two independent channels with pass-bands which can be tuned independently to at least two frequencies (e.g., in the range between the lower bound of the 6 dB bandwidth of the contrast agent response and the upper bound of the 6 dB bandwidth of the tissue response or between the lower bound of the 6 dB bandwidth of the tissue response and the upper bound of the 6 dB bandwidth of the contrast agent response), at least two radiofrequency signal demodulators, one for each of the independent channels, and circuits processing the demodulated signals from independent channels into a single output, wherein echoes reflected by the contrast agent present in the tissue are significantly enhanced in comparison to those reflected by the tissue itself (or vice versa). The separation into independent channels may be carried out using conventional variable bandpass filters or spectrum analyzers with different processing algorithms e.g. fast Fourier, short-time Fourier, wavelet, or Chirp-Z transformations.

The invention also includes a device for processing ultrasound echoes reflected from tissue containing contrast agent as radiofrequency signals including at least two independent channels with pass-bands that can be tuned independently to pre-selected (pre-determined) frequencies, and at least two radiofrequency demodulators, one for each channel. Three or four independent channels would yield better images yet; however, addition of channels increases complexity of the system and choice of the number of channels will be a compromise between image quality and complexity of the system.

Use of the system for ultrasonic imaging of tissue or organs of human and animal patients is also part of this invention.

BRIEF DESCRIPTION OF THE DRAWINGS

These, as well as other objects and advantages of this invention, will be more completely understood and appreciated by careful study of the following more detailed description of a presently preferred exemplary embodiment of the invention taken in conjunction with the accompanying drawings, of which.

DETAILED DESCRIPTION OF THE DRAWINGS

Important aspects of the invention are based on the unexpected finding that enhanced images of organs and tissue are obtained by detection of ultrasound backscatter of a region containing a contrast agent using a realtime method in which ultrasound beams projected to a zone of the tissue to be imaged and echoes reflected from the tissue, received and converted to radiofrequency response signals are processed through at least two independent channels with pass-bands tuned at selected frequencies. Each of the pass-bands is tuned to a different pre-selected frequency which, depending on the nature of the contrast agent and the tissue imaged, is selected among frequencies in the range which enhances the difference between tissue responses and contrast agent responses while still providing detectable signal levels at both frequencies (e.g., between about the lower bound of the 6 dB bandwidth of the contrast agent response and about the upper bounds of the 6 dB bandwidth of the tissue response for the case where the contrast agent resonance frequency is lower than the maximum response of the tissue or, when the resonance frequency of the contrast agent is higher than the maximum response of the tissue, between frequencies found between about the lower bound of the 6 dB bandwidth of the tissue response and about the upper bound of the 6 dB bandwidth of the contrast agent response). The 6 dB amplitude bandwidth is defined as the range of frequencies where the response amplitude remains higher than 50% of its maximum amplitude.

The signals separated into independent channels are then modulated and processed into a single output signal wherein the echoes reflected by the contrast agent present in the tissue are significantly enhanced in comparison to those reflected by the tissue itself i.e., tissue without contrast agent. The output signal is then conventionally stored in a video scan converter and the tissue is regularly scanned in the same manner to produce a realtime video image of the region under investigation. Scanning to produce a video image here has its conventional meaning i.e., that the ultrasonic energy is directed sequentially along previously defined scan lines and the frequency dependent characteristics of the reflected echoes are received and processed a plurality of times for imaged voxel along each scan line. The process is then repeated a plurality of times for a plurality of lines making-up each video image.

Clearly, the realtime method of this invention is effective only with organs or tissue containing contrast agent, since imaging of organs and tissue in the absence of contrast agent provides no advantage over conventional ultrasound imaging.

It has been established that the greater the number of independent frequency-dependent processing channels, the better the resulting image can be. Thus, simulated systems operating with at least three pre-selected frequencies showed better resolution than systems operated with only two. However, there are practical limits to an increased number of independent channels to be used. Increasing the number beyond four, although resulting in further possible improvement of the image, substantially increases complexity of the method and system, thereby increasing the cost and complicating signal processing.

The term "tissue itself" or tissue without contrast agent means sections of tissue inaccessible to the contrast agent i.e., tissue not perfused by contrast agent administered to the patient. On its way through the tissue and back, the ultrasound wave projected to a region to be imaged will pass through segments or so sections perfused with contrast agent and other segments or sections without contrast agent. This should not be confused with known imaging of the same organ or tissue before and after administration of a contrast agent. Here, during the imaging, the contrast agent is always present but the perfused and non-perfused zones are distinguished.

By the tissue response, it is meant the round-trip transfer of energy as a function of frequency, including electrical excitation, electro-acoustic transduction, ultrasonic propagation and reflection within the tissue, acousto-electric transduction and radiofrequency amplification and other signal processing in general.

One fundamental principle underlying the new imaging of this invention is based on exploitation of frequency-dependent behaviors of ultrasound contrast agents. In essence, these imaging principles rely on or exploit certain physical characteristics or "signatures" of contrast agent responses, allowing increased contrast with respect to tissue background. Physical characteristics of the agents studied are found to be linked to their composition to the extent that the contrast agent signatures is found to be the closest analogy to experimental observations. The contrast enhancement described is much larger than what is determined from direct echo amplitude monitoring and its potential is considerable.

A further advantage of the invention comes from the fact that the parameters exploited, per se, do not require any nonlinearity, i.e. they do not require the contrast agent to behave in a non-linear fashion as the required signal processing algorithms are not dependent on excitation of the contrast agent at predetermined levels. Instead, it can operate either in linear or non-linear response conditions.

It is important that the frequencies are selected so that differences between the amplitude of echoes reflected from tissue containing contrast agent and that of echoes reflected by the tissue itself (i.e., without contrast agent), or their ratio, is maximal. This may be achieved, for example, when the frequencies are selected as explained above. Conveniently, one of the selected frequencies may be the resonant frequency of the contrast agent while the other (or others) will be higher or lower. The second selected frequency will be higher for the case in which the contrast agent resonance frequency is lower than the maximum of the tissue response and it will be exactly the opposite in the case in which the tissue maximum response is lower than the contrast agent resonance frequency.

Experiments with contrast agents with different echographic resonant frequencies have shown that, in a majority of cases, the contrast agent resonant frequency is lower than the maximum frequency of the tissue response. However, cases in which this is the other way round are also possible. In any event, whether one deals with the first or the second case, electronic signals corresponding to received echoes are passed through different independent frequency-selective signal processing channels after which they are demodulated. The demodulated, independent channel signals are then processed as a single output signal in a convenient way, e.g., by signal division, subtraction, addition or a combination thereof. Typically, the processing is performed to provide a maximal difference of processed signal amplitude resulting from echoes reflected from tissues containing contrast agent and that of echoes reflected by tissue without contrast agent. By way of illustration, the processed output signal $S_{out}$ (which may thereafter be converted to a video image in the usual way) in response to input spectral components $S(f_1)$, $S(f_2)$, $S(f_3)$, etc. (i.e., the signal output of each individual echo measurement frequency channel) may be provided as a signal proportional to one of the following:

$S_{out} = S(F_1) - S(f_2)$, $S_{out} = [S(f_1) - S(f_2)]/S(f_1)$, $S_{out} = [S(f_1) - S(f_2)]/S(f_2)$, $S_{out} = 2[S(f_1) - S(f_2)]/[S(f_1) + S(f_2)]$, $S_{out} = \{[S(f_1) - S(f_2)]/2 - S(f_3)\}/S(f_1) + S(f_2)]/2\}$, $S_{out} = \{[S(f_1) - S(f_2)]/2 - S(f_3)\}/S(f_3)$, $S_{out} = S(f_1)/S(f_2)$, $S_{out} = \ln S(f_1) - \ln S(f_2)$, or any combinations of the above. In all cases, the following options can apply:

a) if $S_{out}<0$, then $S_{out}$ is set to zero b) if $S_{out}<0$, then $S_{out}$ is replaced with $|S_{out}|$ c) the output signal Sout can be substituted with its natural logarithm, or by any other non-linear function.

d) Any permutation of the components $S(f_1)$, $S(f_2)$, $S(f_3)$ is possible.

e) Any component $S(f)$ can be replaced by its square $S^2(f)$.

f) Any component $S(f)$ can be replaced by its rms average value in a pass-band $D_f$ around $$f: \sqrt{[1/\Delta f]\int S^2(f)df}.$$

g) Any other processing options tending to favor the response around a frequency f in comparison with the response at other frequencies.

It should also be mentioned that the choice of values for the selected or pre-determined frequencies, used for settings of the independent channels (which may be conventional variable bandpass filters, or their equivalents such as spectrum analyzers applying fast Fourier transformation), may be considered as a function of time of arrival of the reflected echoes. This means that since the ultrasound response from the specific organ or tissue imaged depends on the depth it reaches within the body, the quality of the image will depend on the choice of frequencies used. Thus, for deep-seated tissue and organs, better images are obtained with lower frequencies, while organs or tissue closer to the transducer are better imaged with reference frequencies shifted towards higher frequencies.

In another aspect, the invention provides a system for ultrasonic imaging of organs and tissue by detection of ultrasound backscatter of a region containing a contrast agent, the system including an ultrasonic transducer and electronic circuitry for transmitting and receiving ultrasonic signals, signal processing circuits, means for storing the processed signals and a display element, in which the signal processing circuits separate the signal into at least two independent channels with pass-bands which can be tuned independently to at least two frequencies in a range chosen to enhance contrast between tissue responses and contrast agent responses (e.g., between the lower bound of the 6 dB bandwidth of the contrast agent response and the upper bound of the 6 dB bandwidth of the tissue response and the upper bound of the 6 dB bandwidth of the contrast agent response), at least two radiofrequency demodulators, one for each of the independent channels, and a means for processing the demodulated signals from independent channels into a single output wherein the echoes reflected by the contrast agent present in the tissue are significantly enhanced in comparison to those reflected by the tissue itself. The elements for signal separation into independent channels may be conventional variable bandpass filters. As already indicated, systems with three independent channels will perform better than those with only two, and those with four better than those with three; however, the exact number of independent channels used will be determined considering the complexity-to-benefit ratio.

In accordance with alternative embodiments, in place of bandpass filters, the system may have spectral analyzers which are then operated in virtually the same fashion, i.e., using predetermined frequencies as described above regardless of whether the values selected are functions of time of arrival of the reflected echoes or not. The spectral analyzers may process signals using fast Fourier transformation or the Chirp-Z, short-time Fourier or wavelet transformation. The selection of one among these particular processing techniques, or others such as split-spectrum processing, is guided by the requirements imposed by the imaging environment (signal-to-noise ratio, acoustic clutter, axial resolution required, etc.). For example, the applications of wavelet transforms or split-spectrum processing to the ultrasonic detection of flaws in solid materials have demonstrated their potential benefits, in difficult cases where the echoes of interest are similar or lower in amplitude than background clutter (e.g. Xin, J., Muthy, R., Li., X. and Bilgutay, N. M., 1992 IEEE Ultrasonics Symposium). The spectral analyzers may further include a zero crossing detector or an autocorrelation estimator. The predetermined frequencies are different frequencies (e.g., selected among frequencies found between about (embracing) the lower bound of the 6 dB bandwidth of the contrast agent response and about (embracing) the upper bound of the 6 dB bandwidth of the tissue response or are selected among frequencies found between and about (embracing) the lower bound of the 6 dB bandwidth of the contrast agent response). As already mentioned, the exact range will depend, inter alia, on the two different possible situations explained herein.

Optionally, the system may further include non-linear amplifiers linked to the demodulators and placed between the demodulators and at least one analog subtract/divide amplifier. However, it will always include elements for processing the demodulated signals of each of the independent channels into a single output signal in a way such that the echoes reflected by the contrast agent present in the tissue are significantly enhanced in comparison to those reflected by the tissue without contrast agent. The processing element may include at least one analog (or digital) subtract/divide amplifier (or circuit) for processing of the output signal using one or more of the above exemplified processing methods. As already mentioned, though, the system is not limited to the use of any of these particular signal combination methods as they are given only by way of example.

The system of the invention may include an analog or digital video scan converter, preferably, the signal processing is accomplished by digital electronic circuits, operating on data obtained by Analog-to-Digital Conversion of the ultrasound echo signals. The multi-frequency processing may be used to code the amplitude of the output signal by different video colors, which are then superimposed on an otherwise conventional grey-scale video image obtained by the usual processing applied in B-mode imaging.

Benefits of the method and system disclosed may equally be exploited in systems in which the signal channels are part of a receiver of a pulsed-Doppler ultrasound system, which may further incorporate a spectral video output representing a spectrum of velocity distribution and/or an audible signal output (which is preferably a loudspeaker but it may also be any convenient sound reproducing device). Various useful options may be incorporated in the pulsed-Doppler ultrasound system such as a two-dimensional map of velocity distribution which may further be color coded, or it may incorporate a two-dimensional map of echo-amplitude or energy derived from Doppler echo components from moving targets, optionally at predetermined thresholds for velocities inferior or superior to a given value.

Finally, systems using spectral Fourier transform analysis of the returning echoes may be operated by applying spectral analysis within a sliding time window of the returning echoes.

Yet another aspect of the invention provides an ultrasonic apparatus having an ultrasonic probe for transmitting and receiving ultrasonic signals, signal processing elements, filtering and elements for storing the processed signals and a display element in which the signal processing elements include the device or devices for processing ultrasound echoes described above. The ultrasonic apparatus of the invention is useful for imaging tissue or organs of human and animal patients and is particularly suitable for imaging the cardio-vascular system.

Figure 1:
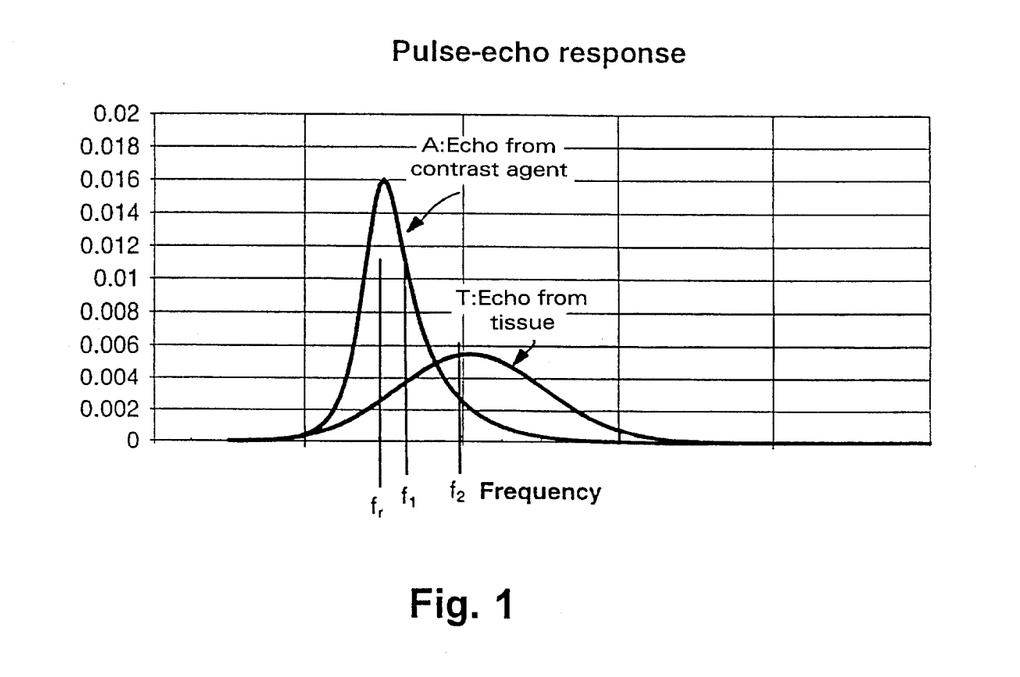
FIG. 1 is a diagram of the pulse-echo frequency response of different reflectors.

In order to further illustrate the disclosed imaging method, it is useful to examine the acoustic energy response expected from various scatterers following propagation in the human body. FIG. 1 illustrates typical frequency responses of a pulse-echo system: the transmit-receive response from tissue, including the electro-acoustic transducer response as well as the differential attenuation in the tissues as a function of frequency, and the transmit-receive response from a contrast agent containing single-size microbubbles. In the present example, $f_r$ is the resonant frequency of the microbubbles found in the contrast agent, and $f_1, f_2$ are frequency components suitably chosen at values different from the value of $f_r$. When the excitation amplitude is such that non-linear oscillation occurs, energy is also backscattered at frequency of the second harmonic. In FIG. 1, it is important to understand that the curves shown are typical of echo-contrast agents and tissues by themselves. In other words, these curves represent the responses of these respective ultrasound reflectors. In an actual in vivo imaging situation, echo signals are a superposition of responses from various targets, or reflectors, intercepted by the ultrasound beam. Thus, spectra of the corresponding echo signals are also a superposition of spectra of acoustic echoes from individual reflectors.

When spectral signals are received and processed to combine them such as $S_{out}=S(f_r)/S(f_1)$, $S=S(f_1)/S(f_2)$, $S=[S(f_1)-S(f_2)]/S(f_2)$, or any other of the methods already mentioned, echo signals other than those from the contrast agent obviously produce amplitude values at much depressed levels compared to those from the contrast agent. The reason is due to the choice of frequencies $f_1$ and $f_2$, which are such that, for example, the ratio of the amplitude of the tissue response at $f_1$ divided by the amplitude of the tissue response at $f_2$ (i.e., $T(f_1)/T(f_2)$), is much smaller than the ratio of the amplitude of contrast agent response at $f_1$ divided by the amplitude of tissue response at $f_2$ (i.e., $A(f_1)/A(f_2)$).

This type of signal processing can be applied to many imaging modes of standard echographic instruments, such as: mechanical B-mode scanning, linear- or phased-array electronic B-mode scanning, color doppler imaging where image is coded by relative scatterer velocities, or Energy color doppler imaging, where image color is coded by echo amplitude alone, following detection by doppler circuitry that eliminates all echoes from stationary targets.

In practice, the present invention requires frequency components to be extracted from raw, radiofrequency, echo signals. This can be accomplished by either hardware of hardware/software based signal processing circuits, in a variety of configurations, all within the scope of this invention. In the following description, an exemplary hardware embodiment is described, resorting to a dual-channel amplifier equipped with analog bandpass filters to extract echo components at f1 and f2, then computing a ratio of the demodulated signals to generate a video image on the scan-converter. An alternative in a digital circuit would be to implement a Fast Fourier Transform on digitized samples of echo waveforms.

Figure 2:
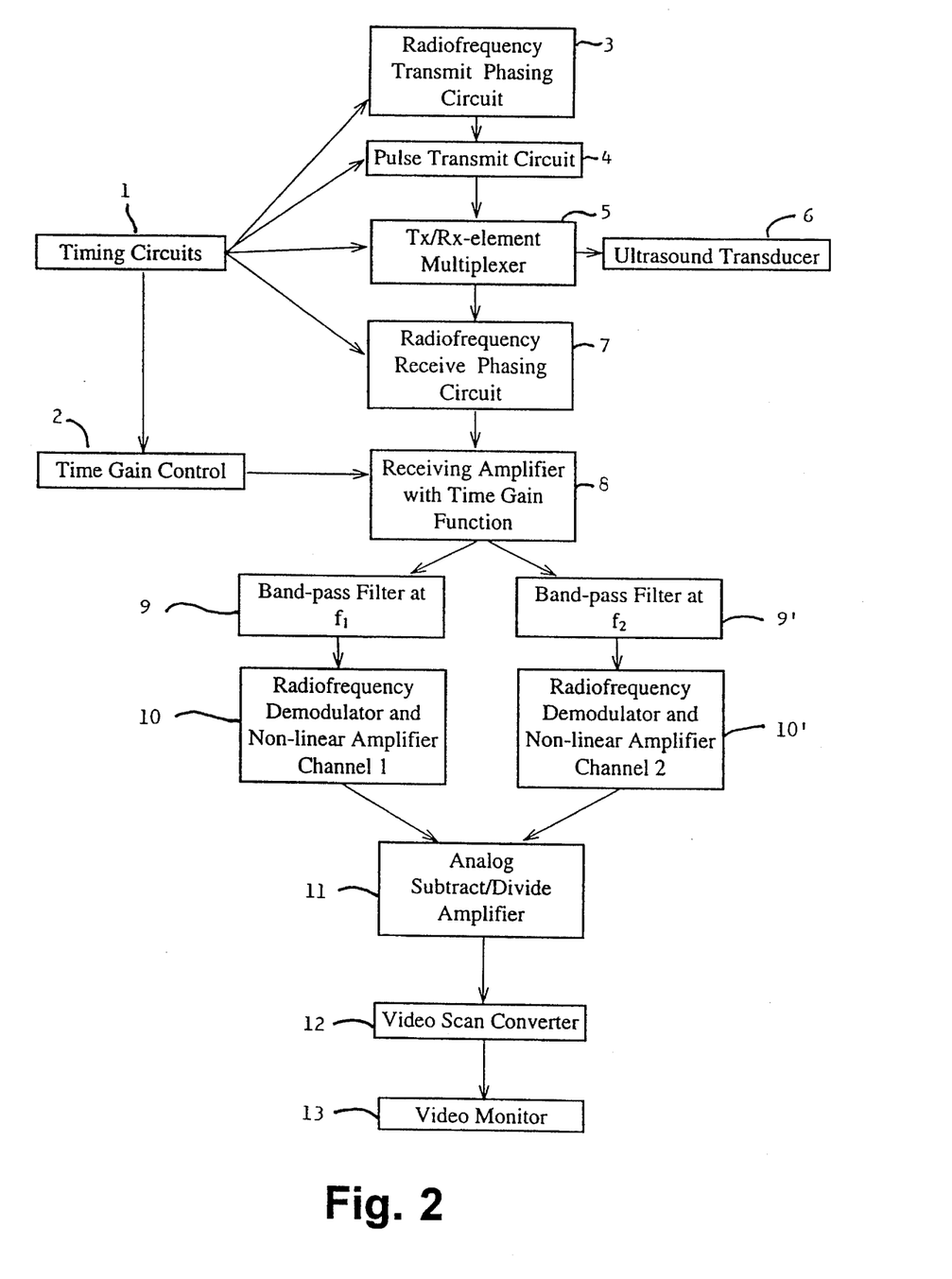
FIG. 2 is a block diagram which illustrates dual-frequency B-mode contrast imaging in a linear array echo-graph according to the invention.

In the analog form, a typical multi-frequency B-mode contrast imaging in a linear array echograph of the invention is outlined in FIG. 2. The echograph typically includes the following components: timing circuits 1, time gain control 2, radiofrequency transmit phasing circuit 3, pulse transmit circuit 4, Tx/Rx-(transmit/receive) element multiplexer 5, ultrasound transducer 6, radio-frequency receive phasing circuit 7, receiving is amplifier with item gain function 8, bandpass filter set to frequency f1–9, bandpass filter set to frequency f2–9', radiofrequency demodulator and non-linear amplifier (channel 1)–10, radiofrequency demodulator and non-linear amplifier (channel 2)–10', analog subtract/divide amplifier—11, video scan converter 12 and video monitor 13.

In operation, timing circuits typically define a pulse-repetition frequency, required for constructing a 2-dimensional echographic image based on sequential scanning of a region to be imaged. For each successive pulse-excitation, timing circuits also define the time-origin of a time-dependent function used to provide variable amplification gain to echo signals originating from increasing imaging depths. This function is realized by the unit called "Time Gain Control," whose output can be a varying voltage, applied to the gain control of a receiving amplifier with adjustable gain. The timing circuits also define transmit phasing, required for the adequate sequential excitation of the individual elements of a linear-array transducer to provide beam focusing and steering, which can take the form of a burst of successive trigger signals, to be applied to a multi-channel electrical excitation circuit ("Pulse Transmit Circuit"). The timing circuits also provide signals needed to bring predefined groups of array-elements into connection with the pulse transmit circuit 4, by way of the connections provided by the transmit-receive element multiplexer.

Focusing and steering of a received ultrasound beam is achieved by the radiofrequency receive phasing circuit 7, whose phase and delay adjustments are also controlled by the timing circuits. Output signals from this receive phasing circuit 7 are then routed to the amplifier with time gain control 8 mentioned previously. It is the output of this amplifier that is fed as a common input to the multiple frequency-selective processing channels described previously for separation of frequency-components in the returning echoes.

The example of FIG. 2 implements frequency separation by feeding echo signals through different bandpass filters, followed by radiofrequency demodulation and non-linear amplification, as is common in conventional echographic instruments. Individual outputs of the multiple processing channels are then routed as input signals to the analog subtract/divide amplifier 11, designed to implement one or more of the various signal processing combining functions previously described, resorting to well-known functionalities of electronic circuitry. The output of that amplifier is then fed to the input of a video scan converter 12, setup, for each sequential pulse, to write incoming data in a pattern corresponding to the selected beam steering and positioning.

Thus, by repeating the above sequence at the specified repetition rate, each time modifying the beam steering and or focusing to obtain echoes from successive positions in organs and tissue, the scan converter 12 output signal refreshes the pixel values of a two-dimensional digital signal image as displayed on video monitor 13, in realtime, i.e., at a rate between a few images per second to hundreds of images per second, sufficient for reproducing perception of movement by the operator of the instrument. In the process described above, regions of the echographic images corresponding to regions containing contrast agent appear with a contrast that is vastly enhanced in comparison to images obtained with conventional instruments in similar imaging conditions.

Figure 3A:
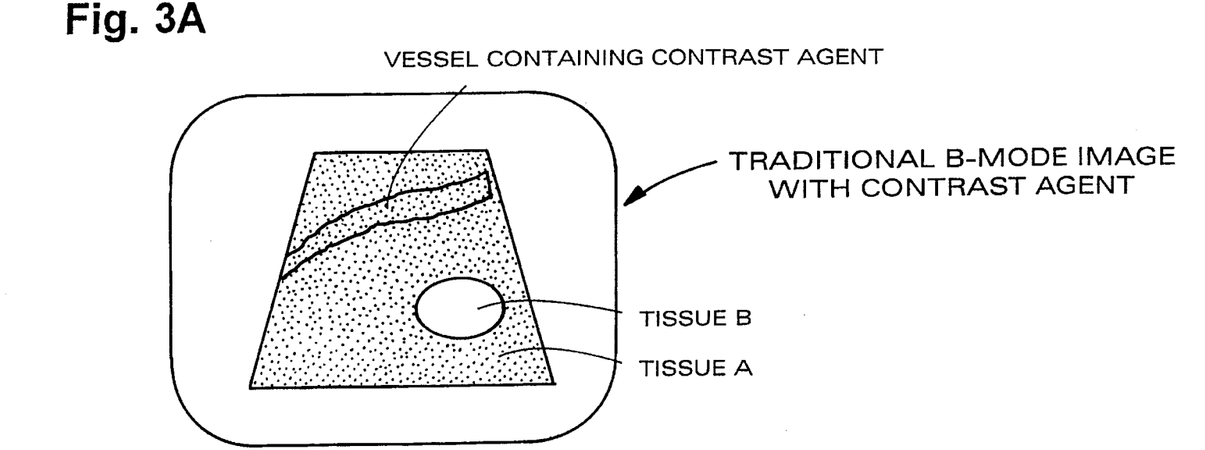
FIGS. 3A and 3B provide an illustration of the multi-frequency contrast image processing of the invention.
Figure 3B:
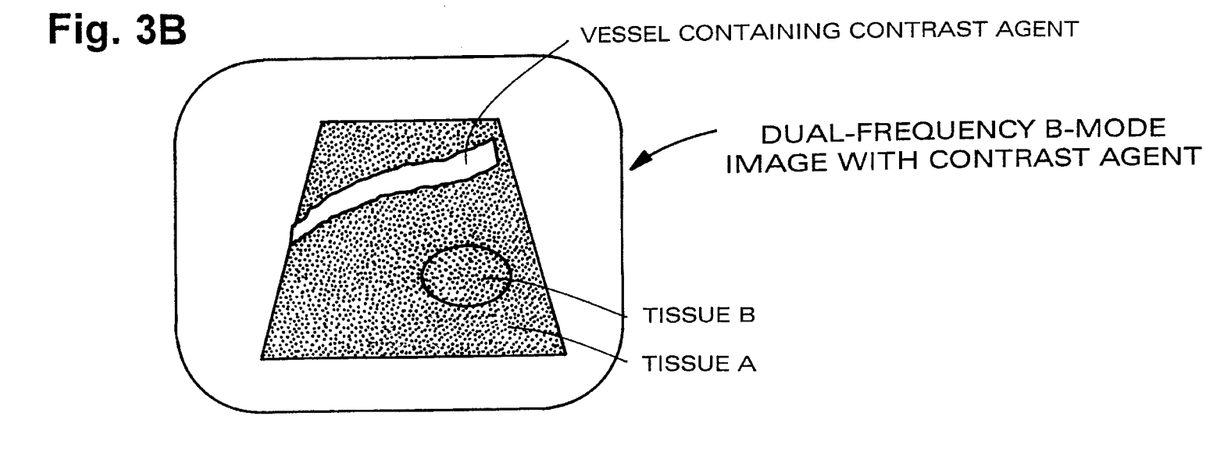

The echographic image resulting from signal processing in accordance with the invention is composed of picture elements (pixels) from the contrast agent with intensity far greater than those arising from echoes from typical tissues, because only the contrast agent has a frequency response signature such that its echo signals are enhanced by the subtract/divide etc. signal processing discussed above. Typically, the effect on a B-mode image is schematically illustrated in FIGS. 3A and 3B. Simulated images for standard B-mode imaging and imaging of the invention in the presence of contrast agent illustrate the effect which may be achieved using this invention. In the illustration, the reference dual-frequency B-mode image in FIG. 3A, means that only two selected frequencies were considered.

As already indicated, similar processing can be applied to Doppler channel processing, for improved contrast enhancement in the cases of two-dimensional Doppler imaging with either velocity-color coding or energy-coding.

The disclosed imaging method exploits the frequency response of the contrast agent, in a linear backscattering mode, which is a typical function differing significantly from the frequency response of tissue alone. In the context of this description, the term "imaging" is used indiscriminately in the context of ultrasound B-mode imaging (pixel intensity dependent on echo-intensity independently of motion), Color Doppler Energy (pixel color or intensity dependent on echo-intensity for targets with relative velocity above or below a certain threshold), or Color Doppler processing (pixel coloring as a function of relative target velocity).

This invention is applicable to all systems for detection of tissue perfusion using an ultrasound contrast agent and to the electronic circuits found in echographic imaging instruments, such as those used for medical diagnosis. Its implementation requires the injection of specific contrast agents in the body, or more generally in the region imaged.

Although only a few exemplary embodiments of this invention have been described in detail, those skilled in the art will recognize that many variations and modifications of these embodiments may be practiced while still enjoying novel features and advantages of the invention. Accordingly, all such variations and modifications are intended to be included within the scope of the appended claims.

What is claimed is:

1. An ultrasonic imaging method for ultrasonic imaging of tissues located in a tissue image region including a contrast agent in at least a portion of said tissue image region, said method comprising the steps of:
    (a) projecting an ultrasound beam into said tissue image region;
    (b) receiving ultrasound reflections from said tissue image region and transducing said reflections into corresponding electrical echo signals;
    (c) first processing said electrical echo signals to derive a plurality of frequency component signals, each frequency component signal representing an electrical echo signal parameter associated with a pre-determined frequency component of said electrical echo signals;
    (d) second processing said plural frequency component signals to combine them into a single enhanced contrast image data signal;
    (e) repeating steps (a) through (d) to derive an ordered array of enhanced contrast image data signals representing an image of said tissue image region; and
    (f) displaying said ordered array of enhanced contrast image data signals as a visual image of said tissue image region.

2. An ultrasonic imaging method as in claim 1 wherein said predetermined frequency components are located within the 6 dB amplitude bandwidths of electrical echo signals produced by said tissue with and without said contrast agent being present.

3. An ultrasonic imaging method as in claim 2 wherein said predetermined frequency components include the peak resonant frequency component of one of (i) said tissue with contrast agent or (ii) said tissue without contrast agent.

4. An ultrasonic imaging method as in claim 1 wherein, said first and second processing steps include the processing of digital signals.

5. An ultrasonic imaging method as in claim 1 wherein said first and second processing steps include the processing of analog signals.

6. An ultrasonic imaging method as in claim 1 wherein said first processing step includes passing said electrical echo signals in parallel through frequency bandpass filters.

7. An ultrasonic imaging method as in claim 1 wherein said first processing step includes converting said electrical echo signals to digital format and subjecting resulting digital signals to digital Fourier analysis, chirp-Z, short-time Fourier or wavelet transformation, or split-spectrum processing.

8. A device for processing of ultrasound echoes reflected from tissue containing contrast agent as radiofrequency signals by the method of claim 1, characterized in that it comprises:
    elements for separating the received response signal into at least two independent channels with pass-bands which can be tuned independently to pre-determined frequencies, and
    at least two radiofrequency demodulators, one for each said channel.

9. The device of claim 8 including elements for separating the response signal into at least three independent channels.

10. A realtime method of ultrasonic imaging of organs and tissue by detection of ultrasound backscatter of a region containing a contrast agent, the method comprising:
    projecting an ultrasound beam to a zone of tissue to be imaged,
    receiving the echo reflected from the tissue as a radiofrequency response signal,
    processing the radiofrequency response signal into a video output by
        (a) passing the response signal to at least two independent channels with frequency pass-bands respectively tuned to one of at least two selected frequencies in a range lying between the lower and upper bounds of (i) the 6 dB bandwidth of the contrast agent response and (ii) the 6 dB bandwidth of the tissue response, and
        (b) demodulating signals passing each of said independent channels and processing the resulting demodulated signals to combine them into a single output signal wherein the echoes reflected by tissues containing contrast agent are significantly enhanced in comparison to those echoes reflected by tissue without contrast agent,
    storing the output in a video scan converter, and
    scanning the tissue to produce a video image of a region under investigation.

11. The method of claim 10 wherein said frequencies are selected so that the difference of echo amplitude reflected from tissue containing contrast agent and that reflected by tissue without contrast agent, or their ratio, is maximal.

12. The method of claim 10 wherein the response signal is passed through at least three respectively corresponding independent channels.

13. The method of claim 10 wherein one of the selected frequencies is the resonant frequency of the contrast agent.

14. The method of claim 10 wherein the values of the selected frequencies are a function of time-of-arrival of the reflected echoes.

15. The method of claim 10 wherein the demodulated channel signals are processed by division, subtraction, addition or a combination thereof.

16. An ultrasonic imaging system for ultrasonic imaging of tissues located in a tissue image region including a contrast agent in at least a portion of said tissue image region, said system comprising:
(a) means for projecting an ultrasound beam into said tissue image region;
(b) means for receiving ultrasound reflections from said tissue image region and transducing said reflections into corresponding electrical echo signals;
(c) means for first processing said electrical echo signals to derive a plurality of frequency component signals, each frequency component signal representing an electrical echo signal parameter associated with a predetermined frequency component of said electrical echo signals;
(d) means for second processing said plural frequency component signals to combine them into a single enhanced contrast image data signal;
(e) means for repeatedly operating means (a) through (d) to derive an ordered array of enhanced contrast image data signals representing an image of said tissue image region; and
(f) means for displaying said ordered array of enhanced contrast image data signals as a visual image of said tissue image region.

17. An ultrasonic imaging system as in claim 16 wherein said predetermined frequency components are located within the 6 dB amplitude bandwidths of electrical echo signals produced by said tissue with and without said contrast agent being present.

18. An ultrasonic imaging system as in claim 17 wherein said predetermined frequency components include the peak resonant frequency component of one of (i) said tissue with contrast agent or (ii) said tissue without contrast agent.

19. An ultrasonic imaging system as in claim 16 wherein, said means for first and second processing include means for processing of digital signals.

20. An ultrasonic imaging system as in claim 16 wherein said means for first and second processing include means for processing of analog signals.

21. An ultrasonic imaging system as in claim 16 wherein said means for first processing includes plural frequency bandpass filters.

22. An ultrasonic imaging system as in claim 16 wherein said means for first processing includes means for converting said electrical echo signals to digital format and subjecting resulting digital signals to digital Fourier analysis, chirp-Z, short-time Fourier or wavelet transformation, or split-spectrum processing.

23. A system for ultrasonic imaging of organs and tissue by detection of ultrasound backscatter of a region containing a contrast agent, the system comprising:

an ultrasonic transducer and electronic circuitry for transmitting and receiving ultrasonic signals, signal processing means including
(a) means for separating the received ultrasonic signal into at least two independent channels with frequency pass-bands which can be tuned independently to one of at least two pre-selected frequencies selected in the range between the upper and lower bounds of (i) the 6 dB bandwidth of the contrast agent response and (ii) the 6 dB bandwidth of the tissue response,
(b) a radiofrequency demodulator for each of said independent channels, and
(c) means for processing the demodulated signals from said independent channels into a single output wherein the echoes reflected by tissue containing contrast agent are significantly enhanced in comparison to those reflected by the tissue itself;

means for storing the processed signals, and a display element connected to display the stored processed signals.

24. The system of claim 23 wherein in the means for separating the received ultrasonic signal includes means for separating it into at least three independent channels.

25. The system of claim 23 including variable bandpass filters or a spectrum analyzer for separating the received ultrasonic signals into said independent channels.

26. The system of claim 25 where spectral Fourier analysis of the returning echoes is applied within a sliding time window on the returning echoes.

27. The system of claim 23 wherein the pre-selected frequencies are functions of time-of-arrival of the reflected echoes.

28. The system of claim 23 wherein the system further comprises a receiving amplifier with a time-gain function connected to supply the received ultrasonic signals to the signal separation elements and non-linear amplifiers connected to process the demodulator outputs.

29. The system of claim 23 wherein the processing means includes at least one analog subtract/divide amplifier for processing the output signal.

30. The system of claim 23 wherein the system includes a video scan converter.

31. The system of claim 23 wherein said signal processing means includes digital electronic circuits operating on data obtained by analog-to-digital conversion of the received ultrasound echo signals.

32. The system of claim 23 where the signal processing means includes means for coding the amplitude of processed output signals by different video colors superimposed on an otherwise conventional grey-scale video image obtained by processing in B-mode imaging.

33. The system of claim 23 wherein said signal processing means are part of a receiver of a pulsed-Doppler ultrasound system.

34. The system of claim 33 wherein the pulsed-Doppler ultrasound system incorporates an audible signal output by means of a loudspeaker.

35. The system of claim 33 wherein the pulsed-Doppler ultrasound system incorporates a spectral video output representing a spectrum of velocity distribution.

36. The system of claim 33 wherein the pulsed-Doppler ultrasound system incorporates a two-dimensional map of velocity distribution.

37. The system of claim 36 wherein the two-dimensional map of velocity distribution is color coded.

38. The system of claim 33 wherein the pulsed-Doppler ultrasound system incorporates a two-dimensional map of echo-amplitude or energy derived from Doppler echo components from moving targets.

39. The system of claim 33 wherein the pulsed-Doppler ultrasound system incorporates a two-dimensional map of Doppler echo components from targets moving with a velocity inferior to a predetermined threshold.

40. The system of claim 33 wherein the pulsed-Doppler ultrasound system incorporates a two-dimensional map of Doppler echo components from targets moving with a velocity superior to a predetermined threshold.

41. Use of the ultrasonic system of claim 23 for imaging of tissue or organs of human and animal patients.

42. Use of the ultrasonic system of claim 23 for imaging of a cardio-vascular system of human and animal patients.

* * * * *